(12) United States Patent
Nakamura et al.

(10) Patent No.: US 7,053,219 B2
(45) Date of Patent: May 30, 2006

(54) ISOXAZOLOPYRIDONE DERIVATIVES AND THEIR USE

(75) Inventors: Masayuki Nakamura, Tsukuba (JP); Hideki Kurihara, Tsukuba (JP); Mitsuru Ohkubo, Tsukuba (JP); Naohiro Tsukamoto, Tsukuba (JP)

(73) Assignee: Banyu Pharmaceutical Co. Ltd. (JP)

( * ) Notice: Subject to any disclaimer, the term of this patent is extended or adjusted under 35 U.S.C. 154(b) by 47 days.

(21) Appl. No.: 10/732,988

(22) Filed: Dec. 10, 2003

(65) Prior Publication Data

US 2004/0176407 A1    Sep. 9, 2004

Related U.S. Application Data

(63) Continuation-in-part of application No. PCT/JP02/05898, filed on Jun. 13, 2002.

(30) Foreign Application Priority Data

Jun. 14, 2001   (JP) .............................. 2001-179801

(51) Int. Cl.
*C07D 471/22* (2006.01)
*A61K 31/44* (2006.01)

(52) U.S. Cl. ........................ 546/116; 546/115; 514/302

(58) Field of Classification Search ................ 546/116, 546/115; 514/302
See application file for complete search history.

(56) References Cited

U.S. PATENT DOCUMENTS

| | | | |
|---|---|---|---|
| 4,049,813 A * | 9/1977 | Nadelson ..................... | 514/302 |
| 4,064,251 A * | 12/1977 | Nadelson ..................... | 514/334 |
| 4,113,727 A * | 9/1978 | Denzer et al. .............. | 544/362 |
| 4,179,566 A | 12/1979 | Nadelson | |
| 4,530,927 A | 7/1985 | Winters et al. | |
| 5,958,931 A | 9/1999 | Adam et al. | |

FOREIGN PATENT DOCUMENTS

| | | |
|---|---|---|
| JP | 51-113877 | 10/1976 |
| JP | 9-227534 | 9/1997 |
| WO | WO 2003015780 A2 * | 2/2003 |

* cited by examiner

*Primary Examiner*—D. Margaret Seaman
(74) *Attorney, Agent, or Firm*—Frommer Lawrence & Haug; Thomas J. Kowalski

(57) ABSTRACT

The invention relates to isoxazolopyridone derivatives of a formula (I-a):

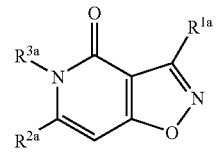

wherein $R^{1a}$ represents an optionally-substituted heteroaryl or phenyl group, $R^{2a}$ represents an optionally-substituted phenyl or heteroaryl group, and $R^{3a}$ represents a methyl group, provided that, (1) when $R^{1a}$ is an unsubstituted phenyl group, then $R^{2a}$ must not be a para-substituted phenyl group of which the substituent is any of a methoxy group, a chloro group, a methyl group, a trifluoromethyl group, a fluoro group, a bromomethyl group or a dimethylaminomethyl group, and $R^{2a}$ must not be an unsubstituted heteroaryl group, and (2) when $R^{1a}$ is a 4-tolyl group or a 4-fluorophenyl group, then $R^{2a}$ must not be an unsubstituted phenyl group, a 4-methoxyphenyl group or a 4-fluorophenyl group, or their pharmaceutically-acceptable salts.

The isoxazolopyridone derivatives or their pharmaceutically-acceptable salts of the invention have a metabotropic glutamic acid receptor-antagonistic effect, and are useful for remedy of, for example, anxiety disorders, psychosomatic disorders, obsessive-compulsive neurosis, bipolar disorders, melancholia, eating disorders, schizophrenia, multi-infarct dementia, Alzheimer disease, epilepsy, Parkinson disease, Huntington's chorea, pain or retrograde neurosis.

8 Claims, No Drawings

US 7,053,219 B2

ISOXAZOLOPYRIDONE DERIVATIVES AND THEIR USE

This application is a continuation-in-part of International Application PCT/JP02/05898 filed on Jun. 13, 2002 and published as WO02/102807 A1 on Dec. 27, 2002, which application claims priority from Japanese Application No. 2001-179801 filed Jun. 14, 2001.

Each of the foregoing applications, and each document cited or referenced in each of the foregoing applications, including during the prosecution of each of the foregoing applications and ("application cited documents"), and any manufacturer's instructions or catalogues for any products cited or mentioned in each of the foregoing applications and articles and in any of the application cited documents, are hereby incorporated herein by reference. Furthermore, all documents cited in this text, and all documents cited or referenced in documents cited in this text, and any manufacturer's instructions or catalogues for any products cited or mentioned in this text or in any document hereby incorporated into this text, are hereby incorporated herein by reference. Documents incorporated by reference into this text or any teachings therein may be used in the practice of this invention. Documents incorporated by reference into this text are not admitted to be prior art.

It is noted that in this disclosure and particularly in the claims, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

TECHNICAL FIELD

The present invention relates to novel isoxazolopyridone derivatives that are useful as a metabotropic glutamic acid receptor antagonist in the field of medicine, and to their use.

BACKGROUND ART

Glutamic acid is a neurotransmitter that mediates excitation transmission in the central nervous system. In addition to having various functions for neurotransmission, glutamic acid participates in many other important brain functions such as life and death, and differentiation and propagation of neurocytes, development of neurocytes and gliacytes, and plastic change in neurotransmission efficiency of matured or developed brains (Annu. Rev. Biophys. Biomol. Struct., S. Nakanishi, M. Masu, Vol. 23, pp. 319–348, 1994).

Through pharmaceutical and molecular-biological studies, the glutamic acid receptor in the central nervous system of mammals is grouped into two, an ion channel-type glutamic acid receptor and a metabotropic glutamic acid receptor. The ion channel-type glutamic acid receptor comprises a complex of different subunit proteins, and it is an ion channel that is made and broken through ligand bonding. On the other hand, the metabotropic glutamic acid receptor conjugates with GTP-binding protein, and it acts through intracellular second messenger production or ion channel activity control via GTP-binding protein (Brain Res. Rev., S. Nakanishi et al., Vol. 26, pp. 230–235, 1998).

In previous studies, it is reported that metabotropic glutamic acid receptor includes eight different subtypes of metabotropic glutamic acid receptors 1 to 8. These are grouped into three subgroups, depending on their amino acid sequence homology, signal transmission and pharmaceutical properties. Regarding their function for intracellular signal transmission, those of group I (metabotropic glutamic acid receptors 1 and 5) activate phospholipase C, and those of group II (metabotropic glutamic acid receptors 2 and 3) and group III (metabotropic glutamic acid receptors 4, 6, 7 and 8) act for adenylate cyclase activity control to thereby retard cyclic adenosine monophosphate (cAMP) accumulation through forskolin stimulation. Those of group II are selectively activated by LY354740 described in Journal of Medicinal Chemistry, Vol. 42, pp. 1027–1040, 1999; andthoseof group III are by L-AP4. Except metabotropic glutamic acid receptor 6 that specifically exists in the retina, the other receptors are expressed broadly in brain and nervous systems, each showing characteristic intracerebral distribution therein, and it is believed that these receptors individually play their own different physiological roles (Neurochem. Int., D. Shoepp et al., Vol. 24, pp. 439–449, 1994; Eur. J. Pharmacol., J. Pin et al., Vol. 375, pp. 277–294, 1999).

Other various publications mentioned below suggest the usefulness of metabotropic glutamic acid receptor antagonist.

1. Neuroscience, Vol. 19, pp. 955–963, 1999 says that any behavioral change is not seen in metabotropic glutamic acid receptor 7 knockout mice based on the anxiety caused by electric stimulation or other unpleasant stimulation by LiCl.

2. Eur. J. Pharmacol., Vol. 319. , pp. 153–156, 1997 says that, when an antagonist to group III metabotropic glutamic acid receptors, α-methylserine-O-phosphate (MSOP) is administered to the hippocampus of rats, then it relaxes the conflict condition of rats and acts for antianxiety for them.

3. Behavioural Brain Res., Vol. 81, pp. 69–79, 1996 says that the learning disability caused by L-AP4 induction is inhibited by an antagonist to metabotropic glutamic acid receptor, MAP4.

4. Neuropharmacol., Vol. 34, pp. 991–1001, 1995 says that the long-term enhancing phenomenon of synaptic conduction efficiency that is seen in the hippocampus is inhibited by the above-mentioned L-AP4.

5. Neuroreport, Vol. 7, pp. 1469–1474, 1996 says that the above-mentioned L-AP4 has an effect of inducing convulsion.

6. Neuropharmacol., Vol. 38, pp. 1631–1640, 1999 says that, when the above-mentioned L-AP4 is applied to striate body-cultured neurocytes, then it induces death of neurocytes.

7. The Journal of Pharmacology and Experimental Therapeutics (JPET), Vol. 292, pp. 406–414, 2000 says that the above-mentioned L-AP4 administered to lateral nuclei of medulla oblongata increases the level of horizontal motion.

8. Pain, Vol. 85, pp. 183–189, 2000 says that a metabotropic glutamic acid receptor agonist, L-SOP administered to the gray matter in the cerebral aqueduct enhances the algesiogenic reaction owing to formalin administration and the enhancing reaction is blocked by the above-mentioned MSOP.

From the above-mentioned descriptions, metabotropic glutamic acid receptor antagonists are useful for medicines, for example, for various mental disorders such as anxiety disorders, psychosomatic disorders, obsessive-compulsive neurosis, bipolar disorders, melancholia, eating disorders, schizophrenia, epilepsy; various types of dementia or attention/cognition deficit disorders such as Alzheimer disease, multi-infarct dementia; retrograde dyskinesia such as Parkinson disease, Huntington's chorea, amyotrophic lateral sclerosis; neurological disorders or neuropathy owing to, for example, cerebral infarction, transient ischemic attack, or wound in the head; and acute or persistent pain in cancer, etc.

Isoxazolopyridone skeleton-having compounds that have structural relation to the compounds of the invention are described in, for example, JP-A 51-113877 (hereinafter referred to as reference A) and JP-A 52-19675 (hereinafter referred to as reference B). Reference A says that isoxazolopyridone derivatives have a blood lipid depressing effect. Reference B illustrates isoxazolopyridone derivatives as intermediates for medicines. However, references A and B do neither say nor suggest that isoxazolopyridone derivatives might have a function as antagonist and/or agonist for metabotropic glutamic acid receptors.

DISCLOSURE OF THE INVENTION

An object of the present invention is to provide a novel metabotropic glutamic acid receptor antagonist that is useful for medicines for, for example, anxiety disorders, psychosomatic disorders, obsessive-compulsive neurosis, bipolar disorders, melancholia, eating disorders, schizophrenia, multi-infarct dementia, Alzheimer disease, epilepsy, Parkinson disease, Huntington's chorea, pain or retrograde neurosis.

We, the present inventors have assiduously studied to solve the above-mentioned problem and, as a result, have found that novel isoxazolopyridone derivatives of the following formula [I-a] or their salts may act as a metabotropic glutamic acid receptor antagonist, and have completed the invention.

Specifically, the invention relates to novel isoxazolopyridone derivatives of a general formula [I-a]:

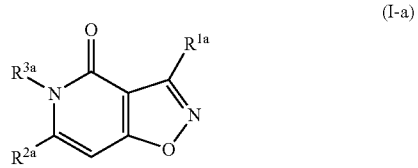

wherein $R^{1a}$ represents an optionally-substituted heteroaryl or phenyl group, $R^{2a}$ represents an optionally-substituted phenyl or heteroaryl group, and $R^{3a}$ represents a methyl group, provided that, (1) when $R^{1a}$ is an unsubstituted phenyl group, then $R^{2a}$ must not be a para-substituted phenyl group of which the substituent is any of a methoxy group, a chloro group, a methyl group, a trifluoromethyl group, a fluoro group, a bromomethyl group or a dimethylaminomethyl group, and $R^{2a}$ must not be an unsubstituted heteroaryl group, and (2) when $R^{1a}$ is a 4-tolyl group or a 4-fluorophenyl group, then $R^{2a}$ must not be an unsubstituted phenyl group, a 4-methoxyphenyl group or a 4-fluorophenyl group, or their pharmaceutically-acceptable salts, and to their use.

The meanings of the abbreviations used herein are mentioned below.
DMSO: dimethylsulfoxide
DMF: N,N-dimethylformamide
DCC: dicyclohexylcarbodiimide
CDI: carbonyldiimidazole
NCS: N-chlorosuccinimide
TFA: trifluoroacetic acid
THF: tetrahydrofuran
PyBrop: bromotripyrrolidinophosphonium hexafluorophosphate The meanings of the terms used herein are mentioned below, and the invention is describe in more detail hereinunder.

"Medicines" means those that are used for remedy and/or prevention of various diseases and disorders.

"Lower alkyl group" means a linear or branched alkyl group preferably having from 1 to 6 carbon atoms, and it includes, for example, a methyl group, an ethyl group, a propyl group, an isopropyl group, a butyl group, an isobutyl group, a sec-butyl group, a tert-butyl group, a pentyl group, an isoamyl group, a neopentyl group, an isopentyl group, a 1,1-dimethylpropyl group, a 1-methylbutyl group, a 2-methylbutyl group, a 1,2-dimethylpropyl group, a hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,2,2-trimethylpropyl group, and a 1-ethyl-2-methylpropyl group.

"Lower alkoxy group" means a group that is derived from a hydroxyl group by substituting its hydrogen atom with the above-mentioned lower alkyl group, and it includes, for example, a methoxy group, an ethoxy group, a propoxy group, an isopropoxy group, a butoxy group, a sec-butoxy group, a tert-butoxy group, a pentyloxy group, an isopentyloxy group, a hexyloxy group, and an isohexyloxy group.

"Aralkyl group" means the above-mentioned lower alkyl group that has the above-mentioned aryl group, including, for example, a benzyl group, a 1-phenylethyl group, a 2-phenylethyl group, a 1-naphthylmethyl group, and a 2-naphthylmethyl group.

"Heteroaryl group" means a 4- to 7-membered monocyclic group having from 1 to 3 hetero atoms selected from a group consisting of oxygen atom, sulfur atom and nitrogen atom, or a condensed heteroaryl group of the monocyclic group that is condensed with a benzene or pyridine ring, and it includes, for example, a furyl group, a thienyl group, a pyrrolyl group, an imidazolyl group, a pyrazolyl group, an isothiazolyl group, an isoxazolyl group, a pyridyl group, a pyrimidinyl group, a quinolyl group, an isoquinolyl group, a quinazolyl group, a quinolidinyl group, a quinoxalinyl group, a cinnolinyl group, a benzimidazolyl group, an imidazopyridyl group, a benzofuranyl group, a naphthyridinyl group, a 1,2-benzisoxazolyl group, a benzoxazolyl group, a benzothiazolyl group, an oxazolopyridyl group, an isothiazolopyridyl group, and a benzothienyl group.

"Halogen atom" includes, for example, a fluorine atom, a chlorine atom, a bromine atom, and an iodine atom.

"Lower alkylcarbamoyl group" means a carbamoyl group that is mono-substituted with the above-mentioned lower alkyl group, and it includes, for example, a methylcarbamoyl group, an ethylcarbamoyl group, a propylcarbamoyl group, an isopropylcarbamoyl group, a butylcarbamoyl group, a sec-butylcarbamoyl group, and a tert-butylcarbamoyl group.

"Di-lower alkylcarbamoyl group" means a carbamoyl group that is di-substituted independently with any of the above-mentioned lower alkyl groups, and it includes, for example, a dimethylcarbamoyl group, a diethylcarbamoyl group, an ethylmethylcarbamoyl group, a dipropylcarbamoyl group, a methylpropylcarbamoyl group, and a diisopropylcarbamoyl group.

"Lower alkylamino group" means an amino group that is mono-substituted with the above-mentioned lower alkyl group, and it includes, for example, a methylamino group, an ethylamino group, a propylamino group, an isopropylamino group, a butylamino group, a sec-butylamino group, and a tert-butylamino group.

"Di-lower alkylamino group" means an amino group that is di-substituted with the same or different, above-mentioned lower alkyl groups, and it includes, for example, a dimethylamino group, a diethylamino group, a dipropylamino group, a methylpropylamino group, and a diisopropylamino group.

For more concretely illustrating the isoxazolopyridone derivatives of the invention, the symbols used in the above-mentioned (I-a) are described in more detail with reference to their specific examples.

$R^{1a}$ is an optionally-substituted heteroaryl or phenyl group.

"Optionally-substituted heteroaryl group" for $R^{1a}$ is meant to indicate the above-mentioned heteroaryl group that is substituted or unsubstituted.

The heteroaryl group itself of the "optionally-substituted heteroaryl group" for $R^{1a}$ is, for example, preferably a pyrrolyl group or a pyridyl group of the above-defined "heteroaryl group", more preferably a pyridyl group.

The substituent for the substituted heteroaryl group includes, for example, a lower alkyl group, a nitro group, a halogen atom, an amino group, a cyano group, a hydroxyl group, a lower alkoxy group, a carboxyl group, a carbamoyl group, a lower alkylcarbamoyl group, a di-lower alkylcarbamoyl group, a di-lower alkylamino group, and a lower alkylamino group. One or more such substituents, but preferably one or two such substituents may bond to the position of the heteroaryl group to which they may bond. In case where the group has two or more such substituents, the substituents may be the same or different.

Of the substituents mentioned above, for example, preferred are a methoxy group, an ethoxy group, an isopropyloxy group, a chlorine atom, a methyl group, and an ethyl group.

The "optionally-substituted heteroaryl group" for $R^{1a}$ includes, for example, a 2-pyridyl group, a 3-pyridyl group, a 4-pyridyl group, a 2-pyrrolyl group, a 3-pyrrolyl group, a 4-pyrrolyl group, a 2-methoxy-4-pyridyl group, a 2-methyl-4-pyridyl group, a 2-chloro-4-pyridyl group, a 3-methoxy-4-pyridyl group, a 3-methyl-4-pyridyl group, a 3-chloro-4-pyridyl group, a 6-methoxy-3-pyridyl group, a 6-methyl-3-pyridyl group, a 6-chloro-3-pyridyl group, a 5-methoxy-2-pyridyl group, a 5-methyl-2-pyridyl group, a 5-chloro-2-pyridyl group, a 2-pyrrolyl group, a 3-pyrrolyl group, a 4-methoxy-2-pyrrolyl group, a 4-methyl-2-pyrrolyl group, a 4-chloro-2-pyrrolyl group, a 4-methoxy-3-pyrrolyl group, a 4-methyl-3-pyrrolyl group, and a 4-chloro-3-pyrrolyl group. Of those, preferred are a 2-pyridyl group, a 3-pyridyl group and a 4-pyridyl group.

"Optionally-substituted phenyl group" for $R^{1a}$ means a substituted or unsubstituted phenyl group.

The substituent for the substituted phenyl group includes, for example, a lower alkyl group, a nitro group, a halogen atom, an amino group, a cyano group, a hydroxyl group, a lower alkoxy group, a carboxyl group, a carbamoyl group, a lower alkylcarbamoyl group, a di-lower alkylcarbamoyl group, a di-lower alkylamino group, and a lower alkylamino group. One or more such substituents, but preferably one or two such substituents may bond to the position of the phenyl group to which they may bond. In case where the group has two or more such substituents, the substituents may be the same or different.

Of the substituents mentioned above, for example, preferred are a lower alkoxy group and a methylenedioxy group; and more preferred are a methoxy group and a methylenedioxy group.

For the "optionally-substituted phenyl group" for $R^{1a}$, for example, preferred are a 2-methoxyphenyl group, a 3-methoxyphenyl group, a 4-methoxyphenyl group, a 2-ethoxyphenyl group, a 3-ethoxyphenyl group, a 4-ethoxyphenyl group, and a 3,4-methylenedioxyphenyl group.

For the "optionally-substituted heteroaryl or phenyl group" for $R^{1a}$, therefore, more preferred are, for example, a 2-pyridyl group, a 3-pyridyl group, a 4-pyridyl group, a 2-methoxyphenyl group, a 3-methoxyphenyl group, a 4-methoxyphenyl group, a 2-ethoxyphenyl group, a 3-ethoxyphenyl group, and a 4-ethoxyphenyl group.

"Optionally-substituted phenyl group" for $R^{2a}$ means a substituted or unsubstituted phenyl group.

The substituent for the substituted phenyl group includes, for example, a nitro group, a halogen atom, an amino group, a cyano group, a hydroxyl group, a lower alkoxy group, a carboxyl group, a carbamoyl group, a lower alkylcarbamoyl group, a di-lower alkylcarbamoyl group, and a methylenedioxy group. One or more such substituents, but preferably one or two such substituents may bond to the position of the phenyl group to which they may bond. In case where the group has two or more such substituents, the substituents may be the same or different.

Of the substituents mentioned above, for example, preferred are a lower alkoxy group and a methylenedioxy group; and more preferred are a methoxy group and a methylenedioxy group.

For the "optionally-substituted phenyl group" for $R^{2a}$, for example, preferred are a 2-methoxyphenyl group, a 3-methoxyphenyl group, a 4-methoxyphenyl group, and a 3,4-methylenedioxyphenyl group.

"Optionally-substituted heteroaryl group" for $R^{2a}$ means a substituted or unsubstituted heteroaryl group.

The heteroaryl group itself of the "optionally-substituted heteroaryl group" for $R^{2a}$ is, for example, preferably a pyridyl group.

The substituent for the substituted heteroaryl group includes, for example, a nitro group, a halogen atom, an amino group, a cyano group, a hydroxyl group, a lower alkoxy group, a carboxyl group, a carbamoyl group, a lower alkylcarbamoyl group, and a di-lower alkylcarbamoyl group. One or more such substituents, but preferably one or two such substituents may bond to the position of the heteroaryl group to which they may bond. In case where the group has two or more such substituents, the substituents may be the same or different.

Of the substituents mentioned above, for example, preferred are a lower alkoxy group, and a di-lower alkylamino group.

For the "optionally-substituted heteroaryl group" for $R^{2a}$, for example, preferred are a 5-methoxy-3-pyridyl group, a 5-dimethylamino-3-pyridyl group, a 6-methoxy-3-pyridyl group, a 6-dimethylamino-3-pyridyl group, a 3-methoxy-4-pyridyl group, a 3-dimethylamino-4-pyridyl group, a 2-methoxy-4-pyridyl group, a 2-dimethylamino-4-pyridyl group, a 5-methoxy-2-pyridyl group, a 5-dimethylamino-2-pyridyl group, a 4-methoxy-3-pyridyl group, a 2-methoxy-3-pyridyl group, a 3-methoxy-2-pyridyl group, a 4-methoxy-2-pyridyl group, and a 6-methoxy-2-pyridyl group.

For the "optionally-substituted phenyl or heteroaryl group" for $R^{2a}$, therefore, preferred are, for example, a phenyl group, a 2-methoxyphenyl group, a 3-methoxyphenyl group, a 4-methoxyphenyl group, a 3,4-methylenedioxyphenyl group, a 5-methoxy-3-pyridyl group, a 3-methoxy-4-pyridyl group, a 5-dimethylamino-3-pyridyl group, and a 5-methoxy-2-pyridyl group.

The isoxazolopyridone derivatives of the invention may exist as their pharmaceutically-acceptable salts. The salts include acid-added salts and base-added salts. The acid-added salts include, for example, hydrohalides such as hydrochlorides, hydrofluorides, hydrobromides, hydroiodides; inorganic acid salts such as nitrates, perchlorates, sulfates, phosphates, carbonates; lower alkylsulfonates such as methanesulfonates, trifluromethanesulfonates, ethanesulfonates; arylsulfonates such as benzenesulfonates, p-toluenesulfonates; organic acid salts such as fumarates, succinates, citrates, tartrates, oxalates, maleates; acid added-salts with organic acids such as amino acids, e.g., glutamates, aspartates. The base-added salts include, for example, alkali metal salts with sodium or potassium; alkaline earth metal salts with calcium or magnesium; ammonium salts; and organic base-added salts with guanidine, triethylamine or dicyclohexylamine. In addition, the compounds of the invention may also exist as solvates of their free compounds or salts, preferably hydrates thereof.

Depending on the substituents that they have, the compounds of the invention may exist as stereoisomers or tautomers, such as optical isomers, diastereomers or geometrical isomers. Needless to say, all these isomers are within the scope of the compounds of the invention. Further needless to say, any mixtures of these isomers are also within the scope of the compounds of the invention.

The compounds [I-a] of the invention may be readily produced in any known reaction mode or according to any per-se known method. Preferably, for example, they may be produced according to the following method.

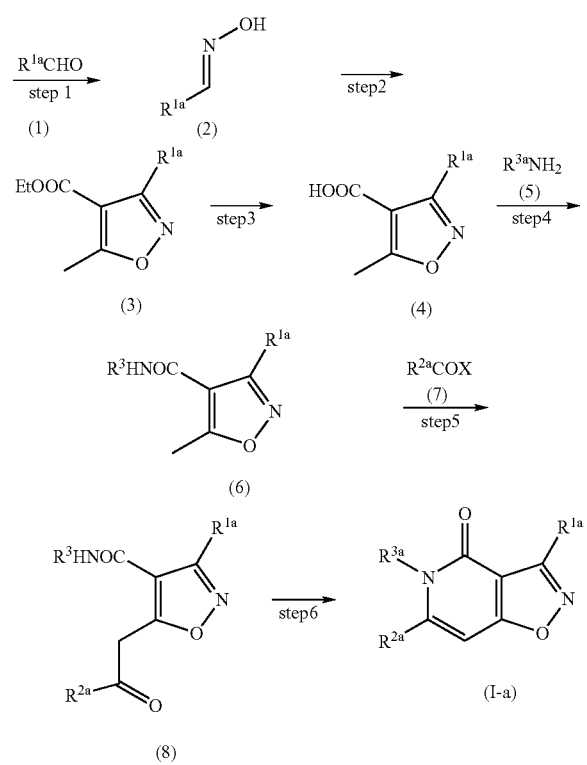

In these formulae, X represents a leaving group, and the other symbols have the same meanings as above.

(Step 1)

In this step, an aldehyde compound (1) is reacted with a hydroxylamine hydrochloride to give a compound (2). The amount of the hydroxylamine hydrochloride to be used is generally from 1 to 2 equivalents relative to one equivalent of the aldehyde compound (1). The reaction solvent includes, for example, MeOH, ethanol, water, DMF, N-methylpyrrolidinone, N-ethylpyrrolidinone, DMSO, and their mixed solvents. Of those, preferred is a mixed solvent of MeOH-water. Thecompound (2) thus obtained is isolated and purified in any known isolation and purification method of, for example, concentration, reduced-pressure concentration, crystallization, solvent extraction, reprecipitation or chromatography; or not isolated and purified, it may be subjected to the next step.

(Step 2)

In this step, the compound (2) obtained in the previous step 1 is reacted with NCS to give a hydroxamic acid chloride compound, and then ethyl 3-pyrrolidine-crotonate is added thereto and the reaction system is reacted with a base to give an isoxazole compound (3). The amount of NCS to be used is generally from 1 to 1.5 equivalents relative to one equivalent of the compound (2). The amount of ethyl 3-pyrrolidine-crotonate also to be used is generally from 1 to 2 equivalents relative to one equivalent of the hydroxamic acid compound. Thus obtained, the compound (3) is isolated and purified in any known isolation and purification method of, for example, concentration, reduced-pressure concentration, crystallization, solvent extraction, reprecipitation or chromatography; or not isolated and purified, it may be subjected to the next step.

(Step 3)

In this step, the compound (3) obtained in the previous step 2 is processed to remove its ethyl group to give a compound (4). This reaction may be effected according to a method described in publications (e.g., Protective Groups in Organic Synthesis, T. W. Green, 2nd Ed., John Wiley & Sons, 1991), or a method similar to the method, or a combination of the method and any other ordinary method. Thus obtained, the compound (4) is isolated and purified in any known isolation and purification method of, for example, concentration, reduced-pressure concentration, crystallization, solvent extraction, reprecipitation or chromatography; or not isolated and purified, it may be subjected to the next step.

(Step 4)

In this step, the compound (4) obtained in the previous step 3 or its reactive derivative is reacted with an amine compound (5) to give a compound (6). The reaction is ordinary amidation that may be effected according to a method described in publications (e.g., Bases and Experiments of Peptide Synthesis, Nobuo Izumiya et al., Maruzen, 1983; Comprehensive Organic Synthesis, Vol. 6, Pergamon Press, 1991), or a method similar to the method, or a combination of the method and any other ordinary method. Concretely, for example, a condensing agent that is well known to those skilled in the art is used for the reaction; or the reaction may be effected in an ester activation method, a mixed acid anhydride method, an acid chloride method or a carbodiimide method that may be carried out by anyone skilled in the art. The amidation reagent includes, for example, DCC, 1-ethoxycarbonyl-2-ethoxy-1,2-dihydroquinoline, 1-cyclohexyl-3-(2-morpholylethyl)carbodiimide, CDI, diphenylphosphoric acid azide, 2-chloro-1,3-dimethyl-2-imidazolium chloride, PyBrop, diethyl cyanophosphate, and 1-ethyl-3-(3-dimethylaminopropyl)carbodiimide hydrochloride. Though varying depending on the type of the compound and the solvent to be used and on the other reaction conditions, the amount of the carboxylic acid or its reactive derivative to be used is generally from 0.5 to 1 equivalent, preferably from 0.5 to 0.8 equivalents relative to one equivalent of the compound (5). Also varying depending on the type of the compound and the solvent to be used and on the other reaction conditions, the amount of the amidation reagent to be used is generally from 1 to 5 equivalents, preferably from 1 to 3 equivalents relative to one equivalent of the carboxylic acid compound (4) or its reactive derivative. The reactive derivative includes, for example, active ester derivatives and active amide derivatives that are generally used in the field of organic chemistry. The reaction solvent includes, for example, methylene chloride, chloroform, THF, diethyl ether, DMF, dimethylacetamide, acetonitrile, and toluene. The reaction time is generally from 1 to 12 hours. Thus obtained, the compound (6) is isolated and purified in any known isolation and purification method of, for example, concentration, reduced-pressure concentration, crystallization, solvent extraction, reprecipitation or chromatography; or not isolated and purified, it may be subjected to the next step.

(Step 5)

In this step, the compound (6) obtained in the previous step 4 is reacted with a compound (7) in the presence of a base to give a compound (8). In the compound (7), X represents a leaving group. The leaving group includes, for example, alower alkoxy group, and a chlorine atom. The base to be used includes, for example, n-butyllithium, lithium diisopropylamide, potassium hexamethyldisilazide, and sodium hexamethyldisilazide. Of those, preferred is n-butyllithium. Though varying depending on the type of the compound and the solvent to be used and on the other reaction conditions, the amount of the base to be used is generally from 2 to 3 equivalents relative to one equivalent of the compound (6). The amount of the compound (7) to be used is generally from 1.5 to 2.5 equivalents relative to one equivalent of the compound (6). The reaction solvent includes, forexample, THF, diethyl ether, and dimethoxyethane. The reaction time is generally from 1 to 5 hours. Thus obtained, the compound (8) is isolated and purified in any known isolation and purification method of, for example, concentration, reduced-pressure concentration, crystallization, solvent extraction, reprecipitation or chromatography; or not isolated and purified, it may be subjected to the next step.

(Step 6)

In this step, the compound (8) obtained in the previous step 5 is heated under reflux in the presence of an.acid for intramolecular cyclization to give a compound (I-a). The acid to be used includes, for example, paratoluenesulfonic acid, hydrochloric acid, and sulfuric acid. Of those, preferred is paratoluenesulfonic acid. Though varying depending on the type of the compound and the solvent to be used and on the other reaction conditions, the amount of the acid to be used is generally from 1 to 2 equivalents relative to one equivalent of the compound (8). The reaction solvent is generally any of THF, dioxane or toluene. The reaction time is generally from 1 to 20 hours, preferably from 1 to 5 hours. Thus obtained, the compound (I-a) is isolated and purified in any known isolation and purification method of, for example, concentration, reduced-pressure concentration, crystallization, solvent extraction, reprecipitation or chromatography.

The compounds (I-a) of the invention may also be produced through solid phase reaction according to the method mentioned below.

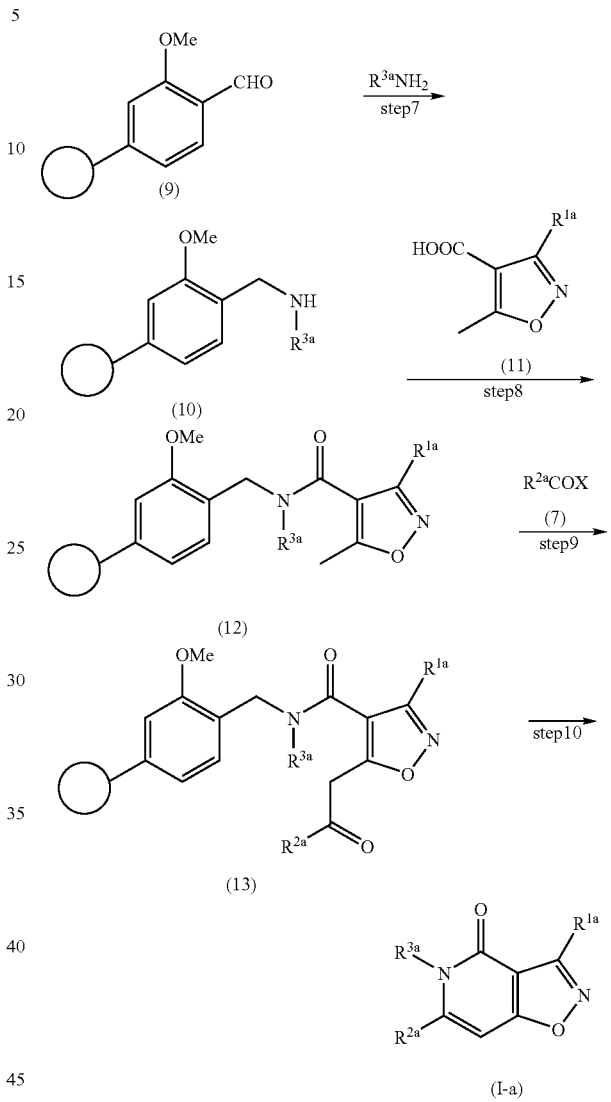

In these formulae, ○ indicates a solid-phase carrier, and the other symbols have the same meanings as above.

(Step 7)

In this step, an aldehyde group-having solid-phase carrier (9) is reacted with a primary amine compound $R^{3a}NH_2$ to give a compound (10). The aldehyde group-having solid-phase carrier is, for example, a commercial product, Argo-Gel-MB-CHO Resin™. This reaction is per-se known reductive amination, and it may be effected according to a method described in publications (e.g., J. Org. Chem., Vol. 60, p. 5742, 1995), or a method similar to the method, or a combination of the method and any other ordinary method. The amine to be used includes, for example, methylamine, ethylamine and propylamine. Of those, preferred is methylamine. Though varying depending on the type of the compound and the solvent to be used and on the other reaction conditions, the amount of the primary amine $R^{3a}NH_2$ to be used is generally from 3 to 10 equivalents relative to one equivalent of the solid-phase carrier (9). The reducing agent to be used includes, for example, NaBH(OAc)$_3$, NaBH$_4$, and NaCNBH$_3$. Of those, preferred is NaBH(OAc)$_3$. The amount of the reducing agent to be used is generally from 3 to 10 equivalents relative to one equivalent of the compound (9). The reaction solvent may be generally any of DMF, THF, methylene chloride, MeOH, ethanol, toluene, benzene, or their mixed solvents. If desired, an acid may be added to the reaction solvent to carry out the reaction, and its amount may be from 1/50 to 1/10 of the reaction solvent. The acid is, for example, acetic acid. Thus obtained, the solid-phase carrier (10) may be washed with any of DMF, MeOH, EtOH, THF, methylene chloride, chloroform or their mixed solvents to remove the excess reagent, etc.

(Step 8)

In this step, the solid-phase carrier (10) obtained in the previous step 7 is reacted with an isoxazole-carboxylic acid (11) or its reactive derivative to give a compound (12). Concretely, the reaction may be ordinary amidation. For example, a condensing agent that is well known to those skilled in the art is used for the reaction; or the reaction may be effected in an ester activation method, a mixed acid anhydride method, an acid chloride method or a carbodiimide method that may be carried out by anyone skilled in the art. The amidation reagent includes, for example, DCC, 1-ethoxycarbonyl-2-ethoxy-1,2-dihydroquinoline, 1-cyclohexyl-3-(2-morpholylethyl)carbodiimide, CDI, diphenylphosphoric acid azide, 2-chloro-1,3-dimethyl-2-imidazolium chloride, PyBrop, diethyl cyanophosphate, and 1-ethyl-3-(3-dimethylaminopropyl)carbodiimide hydrochloride. Of those amidation reagents, preferred is 2-chloro-1,3-dimethyl-2-imidazolium chloride. Though varying depending on the type of the compound and the solvent to be used and on the other reaction conditions, the amount of the carboxylic acid or its reactive derivative to be used is generally from 3 to 10 equivalents, preferably from 3 to 5 equivalents relative to one equivalent of the compound (10). Also varying depending on the type of the compound and the solvent to be used and on the other reaction conditions, the amount of the amidation reagent to be used is generally from 3 to 10 equivalents, preferably from 3 to 5 equivalents relative to one equivalent of the compound (10). The reaction solvent includes, for example, methylene chloride, chloroform, THF, diethyl ether, DMF, dimethylacetamide, acetonitrile, and toluene. The reaction time is generally from 1 to 20 hours. Thus obtained, the solid-phase carrier (12) may be washed with any of DMF, MeOH, EtOH, THF, methylene chloride, chloroform or their mixed solvents to remove the excess reagent, etc.

(Step 9)

In this step, the 5-positioned methyl group of the isoxazole of the solid-phase carrier (12) obtained in the previous step 8 is deprotonated in the presence of a base, and then the deprotonated solid-phase carrier is reacted with an aryl or heteroaryl ester compound (7) to give a compound (13). The base to be used includes, for example, n-BuLi, lithium diisopropylamide, and potassium hexamethyldisilazide. Of those, preferred is potassium hexamethyldisilazide. Though varying depending on the type of the compound and the solvent to be used and on the other reaction conditions, the amount of the base to beused is generally from 3 to 10 equivalents relative to one equivalent of the compound (12). Also varying depending on the type of the compound and the solvent to be used and on the other reaction conditions, the amount of the ester to be used is generally from 3 to 10 equivalents relative to one equivalent of the compound (12).

The aryl or heteroaryl ester compound (7) may have an electron-attractive group or an electron-donating group on the aryl or heteroaryl group thereof. The aryl or heteroaryl ester compound (7) may be produced by reacting a commercially-available arylcarboxylic acid or heteroarylcarboxylic acid with trimethylsilyldiazomethane. Thus obtained, the compound (13) may be washed with any of DMF, MeOH, EtOH, THF, methylene chloride, chloroform or their mixed solvents to remove the excess reagent, etc.

(Step 10)

In this step, the compound (13) obtained in the previous step 9 is reacted with acid for release of an isoxazole derivative from the solid-phase carrier followed by intramolecular cyclization of the derivative to give an isoxazolopyridone derivative (I-a). The reaction to release the derivative from the solid-phase carrier may be effected in an ordinary method of releasing a compound from a solid-phase carrier that is employed in general solid-phase reaction, or according to the method, or a combination of the method with any other method. Concretely, for example, the isoxazolopyridone derivative (I-a) may be produced by processing the compound (13) with an organic acid-containing inert organic solvent at room temperature. The organic acid may be, for example, TFA. The inert organic solvent may be, for example, methylene chloride. The ratio by volume of the organic acid/inert solvent is generally from 10 to 100%, preferably from 20 to 50%. For completing the intramolecular cyclization, for example, the solid-phase carrier is filtered, the resulting filtrate is concentrated under reduced pressure, 90% TFA/methylene chloride is added thereto, and the reaction liquid is stirred at room temperature for 1 to 48 hours, preferably from 2 to 24 hours. Thus obtained, the compound (I-a) is isolated and purified in any known isolation and purification method of, for example, concentration, reduced-pressure concentration, crystallization, solvent extraction, reprecipitation or chromatography.

The compound of formula (I-a) may be formed into its pharmaceutically-acceptable salts in any ordinary manner. Concretely, when the compound of formula (I-a) has a basic group such as an amino group in its molecule, then the compound may be processed with an acid so as to convert it into the corresponding pharmaceutically-acceptable salt thereof. On the other hand, for example, when the substituent of $R^{1a}$ has an acid group such as a carboxyl group, then the compound may be processed with a base whereby it may be converted into the corresponding pharmaceutically-acceptable salt thereof. Further, the salt may be converted into the free compound thereof also in any ordinary manner.

Next described are the metabotropic glutamic acid receptor-antagonistic effect of the compounds of formula (I-a) of the invention and a method for testing the compounds.

The excellent metabotropic glutamic acid receptor-inhibiting effect of the compounds of formula (I-a) of the invention may be verified, for example, according to the following Test Method 1.

(Test Method 1) Metabotropic Glutamic Acid Receptor-Antagonistic Effect:

Using LIPOFECTAMINE (by Gibco BRL), CHO cells were transfected with a CDNA of rat metabotropic glutamic acid receptor 7a, which is described in J. Biol. Chem., N. Okamoto et al., Vol. 269, pp. 1231–1236, 1994, to give a cell strain capable of stably expressing rat metabotropic glutamic acid receptor 7a. The metabotropic glutamic acid receptor 7a-transfected CHO cells were further transfected with a Gα15 cDNA, which is describedin J. Biol. Chem., S. Offermanns, M. I. Simon, Vol. 270, pp. 15175–15180, 1995, to give a cell strain capable of stably expressing rat metabotropic glutamic acid receptor 7a and Gα15. The CHO cells capable of stably expressing metabotropic glutamic acid receptor 7a and Gα15 were incubated along with Fluo-3AM (final concentration 4 µM) at 37° C. for 1 hour, and then washed 4 times with an assay buffer (1×Hanks' salt with 2.5 mM probenecid and 20 mM HEPES (N-2-hydroxyethylpiperazine-N'-2-ethanesulfonic acid), and the resulting cells were assayed for $[Ca^{2+}]_i$. For the determination of $[Ca^{2+}]_i$, used was a fluorimetric imaging plate reader (FLIPR by Molecular Device). Concretely, using an agonist, 0.5 mM L-AP4, the capacity of the antagonistic substance was measured.

The Hanks' salt was prepared by 10-fold diluting a Hanks' balanced solution (Gibuco BRL 14065-056 10×). The final concentration of the Hanks' salt is as follows:

$CaCl_2$: 0.14 g/liter
KCl: 0.4 g/liter
$KH_2PO_4$: 0.06 g/liter
$MgCl_2.6H_2O$: 0.1 g/liter
$MgSO_2.7H_2O$: 0.1 g/liter
NaCl: 8 g/liter
$Na_2HPO_4.7H_2O$: 0.09 g/liter
D-glucose: 1 g/liter Five minutes before the administration of the agonist thereto, a varying concentration of a test compound was administered to the cells.

TABLE 1

Metabotropic Glutamic Acid Receptor-Antagonistic Effect

| Test Compound | $IC_{50}$ (nM) |
|---|---|
| Compound of Production Example 8 | 7.65 |
| Compound of Production Example 32 | 10.45 |

As in Table 1, the compounds of the invention have an excellent metabotropic glutamic acid receptor-antagonistic effect.

The CHO cells stably expressing rat metabotropic glutamic acid receptor 7a were incubated along with an assay buffer (Locke's buffer and 1 mM IBMX (3-isobutyl-1-methylxanthine)) at 37° C. for 10 minutes, and a varying concentration of a test compound was applied to them, and the cells were further incubated for 10 minutes. 20 minutes after the administration of the agonist (0.5 mM L-AP4) and 10 µM forskolin thereto, the intramolecular cAMP of the cells was determined. For the cAMP determination, used was a cAMP EIA system (by Amersham Pharmacia Biotec, Little Chalfont, Buckinghamshire, England).

From the above results, the isoxazolopyridone derivatives of formula (I-a) of the invention are useful for medicines for diseases and disorders in which metabotropic glutamic acid receptor, especially metabotropic glutamic acid receptor 7 may participate, for example, for various mental disorders such as anxiety disorders, psychosomatic disorders, obsessive-compulsive neurosis, bipolar disorders, melancholia, eating disorders, schizophrenia, epilepsy; various types of dementia or attention/cognition deficit disorders such as Alzheimer disease, multi-infarct dementia; retrograde dyskinesia such as Parkinson disease, Huntington's chorea, amyotrophic lateral sclerosis; neurological disorders or neuropathy owing to, for example, cerebral infarction, transient ischemic attack, or wound in the head; and acute or persistent pain in cancer, etc.

The isoxazolopyridone derivatives of formula (I-a) may be orally or parenterally administered. When the compound of the invention is clinically used, pharmaceutically-acceptable additives may be added thereto in accordance with the administration mode for it, to thereby prepare various preparations for administration. The additives may be various ones that are generally used in the field of pharmaceutics, including, forexample, gelatin, lactose, whitesugar, titanium oxide, starch, crystalline cellulose, hydroxypropylmethyl cellulose, carboxymethyl cellulose, corn starch, microcrystalline wax, white petrolatum, magnesium metasilicate aluminate, anhydrous calcium phosphate, citric acid, trisodium citrate, hydroxypropyl cellulose, sorbitol, fatty acid ester, polysorbate, sucrose fatty acid ester, polyoxyethylene hardened castor oil, polyvinylpyrrolidone, magnesium stearate, light silicic anhydride, talc, vegetable oil, benzyl alcohol, gumarabic, propylene glycol, polyalkylene glycol, cyclodextrin and hydroxypropyldextrin.

Regarding their form, the preparations that are formulated along with these additives may take any form of, for example, solid preparations such as tablets, capsules, granules, powders or suppositories; or liquid preparations such as syrups, elixirs or injections. These may be formulated in any ordinary method known in the field of pharmaceutics. The liquid preparations may be prepared through, dissolution or suspension in water or in any other suitable medium just before use. Especially for injections, the ingredients may be dissolved or suspended in physiological saline or sucrose solution, if desired, and buffer and preservative may be added thereto.

These preparations may contain the compound of the invention in a ratio of from 1.0 to 100% by weight, preferably from 1.0 to 60% by weight of the overall amount of the preparation.

In case where the compounds of the invention are used, for example, in the field of clinics, the dose and the administration frequency thereof will vary, depending on the sex, the age, the body weight and the condition of the cases to which they are administered and on the type and the scope of the intended treatment. In general, however, the dose is preferably from 0.1 to 100 mg/kg adult/day for oral administration, and the administration frequency may be from once to a few times a day. For parenteral administration, the dose is preferably from 0.001 to 10 mg/kg adult/day, and the administration frequency may be from once to a few times a day.

BEST MODE FOR CARRYING OUT THE INVENTION

The invention is described more concretely with reference to the following Examples, to which, however, the invention is not limited.

The meanings of the abbreviations in nuclear magnetic resonance spectrometry are mentioned below.

s: singlet
d: doublet
dd: double doublet
t: triplet
m: multiplet
br: broad
q: quintet
J: coupling constant
Hz: hertz

PRODUCTION EXAMPLE 1

Production of 5-methyl-6-(4-methoxyphenyl)-3-pyridin-4-yl-isoxazolo-[4,5c]pyridin-4(5H)-one

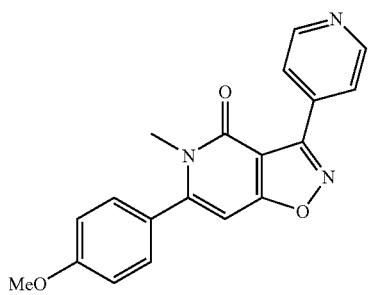

Paratoluenesulfonic acid monohydrate (25 mg) was added to a THF solution (5 ml) of 5-(4-methoxyphenylcarbonyl-methyl)-3-(pyridin-4-yl)-N-methyl-4-isoxazolecarboxamide (52 mg, 0.15 mmols) obtained in Reference Example 6, and the reaction liquid was heated under reflux for 5 hours. The reaction liquid was poured into a mixed solvent of aqueous saturated sodium bicarbonate solution and chloroform, and the organic layer was separated. The organic layer was dried with anhydrous magnesium sulfate, the solvent was evaporated away under reduced pressure, and the remaining residue was purified through silica gel column chromatography (Wakogel® C-300 with eluent solvent of chloroform-MeOH (50:1)) to obtain the entitled compound (30 mg, yield 60%).

The NMR and Mass data of the compound obtained in Production Example 1 are shown below.

$^1$H NMR (300 MHz, CDCl$_3$) δ ppm: 3.45(s, 3H), 3.90(s, 3H), 6.56(s, 1H), 7.03(d, J=8.9 Hz, 2H), 7.34(d, J=8.9 Hz, 2H), 8.30(d, J=6.2 Hz, 2H), 8.80(d, J=6.2 Hz, 2H)

ESI-MS(m/e): (M+H)$^+$=334

According to the method as in Reference Examples 1 to 6 and Production Example 1, or in the same manner as therein, or by combining the method with any other known method, compounds of the following Production Examples 2 to 10 can be produced.

PRODUCTION EXAMPLE 2

Production of 3-(4-chlorophenyl)-5-methyl-6-phenylisoxazolo[4,5c]-pyridin-4(5H)-one:

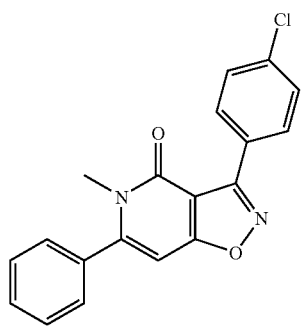

The NMR and Mass data of the compound obtained in Production Example 2 are shown below.

$^1$H NMR (300 MHz, CDCl$_3$) δ ppm: 3.42(s, 3H), 6.55(s, 1H), 7.38–7.44(m, 2H), 7.46–7.56(m, 5H), 8.29–8.34(m, 2H)

ESI-MS(m/e): (M+H)$^+$=337

PRODUCTION EXAMPLE 3

Production of 5-methyl-3-pyridin-4-yl-6-phenyl-isoxazolo[4,5c]pyridin-4(5H)-one:

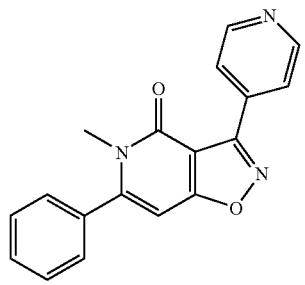

The NMR and Mass data of the compound obtained in Production Example 3 are shown below.

$^1$H NMR (300 MHz, CDCl$_3$) δ ppm: 3.43(s, 3H), 6.59(s, 1H), 7.38–7.46(m, 2H), 7.50–7.58(m, 3H), 8.28–8.33(m, 2H), 8.77–8.83(m, 2H)

ESI-MS(m/e): (M+H)$^+$=304

PRODUCTION EXAMPLE 4

Production of 3-(4-methoxyphenyl)-5-methyl-6-phenylisoxazolo[4,5c]-pyridin-4(5H)-one:

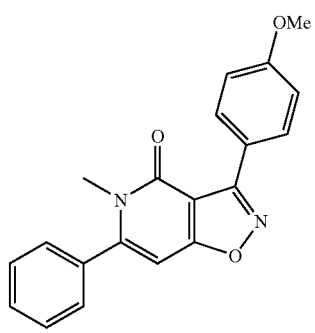

The NMR and Mass data of the compound obtained in Production Example 4 are shown below.

$^1$H NMR (300 MHz, CDCl$_3$) δ ppm: 3.41(s, 3H), 3.88(s, 3H), 6.53(s, 1H), 7.04(d, J=9.0 Hz, 2H), 7.34–7.44(m, 2H), 7.49–7.55(m, 3H), 8.33(d, J=9.0 Hz, 2H)

ESI-MS(m/e): (M+H)$^+$=333

PRODUCTION EXAMPLE 5

Production of 5-methyl-3-pyridin-2-yl-6-phenyl-isoxazolo[4,5c]pyridin-4(5H)-one

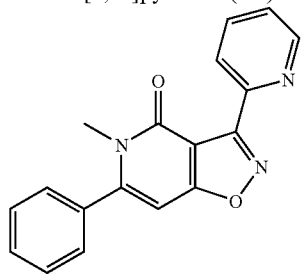

The NMR and Mass data of the compound obtained in Production Example 5 are shown below.

$^1$H NMR (300 MHz, CDCl$_3$) δ ppm: 3.42(s, 3H), 6.58(s, 1H), 7.39–7.46(m, 3H), 7.51–7.57(m, 3H), 7.90(dt, J=1.8 Hz, 7.7 Hz, 1H), 8.58(dt, J=1.1 Hz, 7.7 Hz, 1H), 8.82–8.86 (m, 1H)

ESI-MS(m/e): (M+H)$^+$=304

PRODUCTION EXAMPLE 6

Production of 5-methyl-3-pyridin-3-yl-6-phenyl-isoxazolo[4,5c]pyridin-4(5H)-one

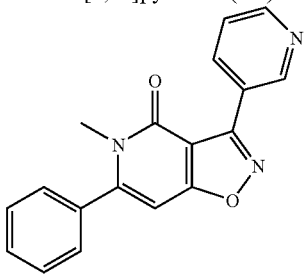

The NMR and Mass data of the compound obtained in Production Example 6 are shown below.

$^1$H NMR (300 MHz, CDCl$_3$) δ ppm: 3.42(s, 3H), 6.58(s, 1H), 7.37–7.48(m, 3H), 7.49–7.58(m, 3H), 8.71–8.79(m, 2H), 9.41–9.46(m, 1H)

ESI-MS(m/e): (M+H)$^+$=304

PRODUCTION EXAMPLE 7

Production of 5-methyl-6-(3-methoxyphenyl)-3-pyridin-4-yl-isoxazolo-[4,5c]pyridin-4(5H)-one:

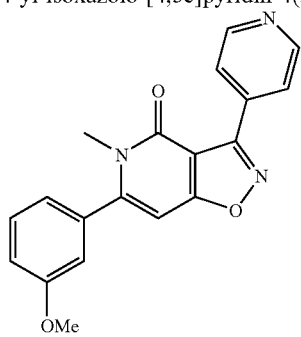

The NMR and Mass data of the compound obtained in Production Example 7 are shown below.

$^1$H NMR (300 MHz, CDCl$_3$) δ ppm: 3.44(s, 3H), 3.87(s, 3H), 6.59(s, 1H), 6.91–6.93(m, 1H), 6.95–7.00(m, 1H), 7.04–7.09(m,1H), 7.42–7.47(m, 1H), 8.30(d, J=6.2 Hz, 2H), 8.80(d, J=6.2 Hz, 2H)

ESI-MS(m/e): (M+H)$^+$=334

PRODUCTION EXAMPLE 8

Production of 5-methyl-3-(2-methoxyphenyl)-6-phenylisoxazolo[4,5c]pyridin-4(5H)-one

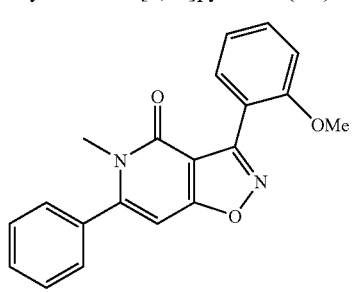

The NMR and Mass data of the compound obtained in Production Example 8 are shown below.

1H NMR (300 MHz, CDCl$_3$)δ ppm: 3.33(s, 3H), 3.87(s, 3H), 6.52(s, 1H), 7.04–7.10(m, 2H), 7.36–7.44(m, 2H), 7.46–7.56(m, 5H)

ESI-MS(m/e): (M+H)$^+$=333

PRODUCTION EXAMPLE 9

Production of 5-methyl-3-(3-methoxyphenyl)-6-phenylisoxazolo[4,5c]-pyridin-4(5H)-one

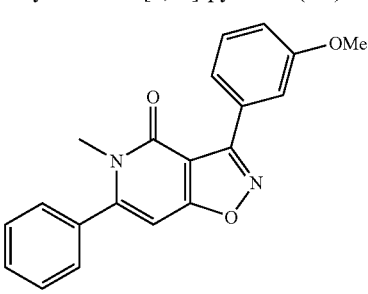

The NMR and Mass data of the compound obtained in Production Example 9 are shown below.

$^1$H NMR (300 MHz, CDCl$_3$) δ ppm: 3.41(s, 3H), 3.91(s, 3H), 6.55(s, 1H), 7.04–7.09(m, 1H), 7.38–7.46(m, 3H), 7.50–7.56(m,3H), 7.91–7.97(m,2H)

ESI-MS(m/e): (M+H)$^+$=333

PRODUCTION EXAMPLE 10

Production of 3-(2-chloro-5-methoxyphenyl)-5-methyl-6-phenylisoxazolo-[4,5c]pyridin-4(5H)-one:

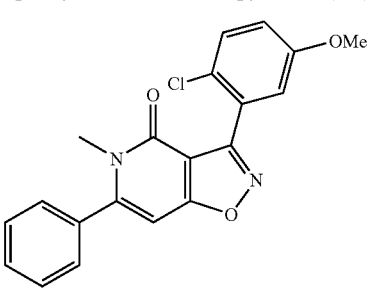

The NMR and Mass data of the compound obtained in Production Example 10 are shown below.

$^1$H NMR (300 MHz, CDCl$_3$) δ ppm: 3.69(s, 3H), 3.82(s, 3H), 6.55(s, 1H), 7.00(dd, J=3.1 Hz, 8.8 Hz, 2H), 7.10(d, J=3.1 Hz, 1H), 7.38–7.42(m, 2H), 7.44(d, J=8.8 Hz, 1H), 7.50–7.55(m, 3H)

ESI-MS(m/e): (M+H)$^+$=367

PRODUCTION EXAMPLE 11

Production of 5-methyl-3-phenyl-6-pyridin-4-yl-isoxazolo[4,5-c]pyridin-4(5H)-one

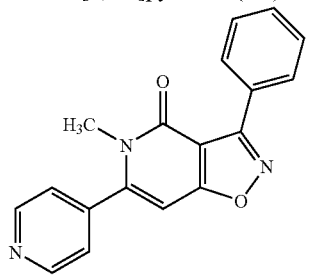

40 mg (0.016 mmols) of the resin obtained in Reference Example 7 was suspended in 0.5 ml of THF, and 1.0 ml of a toluene solution of 0.5 M potassium hexamethyldisilazide was added thereto and stirred at room temperature for 20 minutes. 5.7 mg (5.7 mg, 0.048 mmols) of methyl nicotinate was added to it, and the reaction liquid was further stirred at room temperature for 2 hours. The reaction mixture was filtered, and the residual resin was washed with DMF, MeOH, THF and methylene chloride in that order twice each. A solution of 50% THF/methylene chloride solution was added to the thus-obtained resin, and the reaction liquid was stirred at room temperature for 2 hours. The reaction mixture was filtered and washed with methylene chloride, and the resulting filtrate was concentrated under reduced pressure. A 90% TFA/methylene chloride solution was added to the resulting residue, and the reaction liquid was left at room temperature for 12 hours and then concentrated under reduced pressure to obtain the entitled compound (3.0 mg, yield 63%).

The NMR and Mass data of the compound obtained in Production Example 11 are shown below.

$^1$H NMR (300 MHz, CDCl$_3$) δ ppm: 3.42(3H, s), 6.56(1H, s), 7.36(2H, d, J=6.0 Hz), 7.48–7.55(3H, m), 8.25–8.30(2H, m), 8.83(2H, d, J=6.0 Hz)

ESI-MS(m/e): (M+H)$^+$=304

According to the method as in Production Example 11, or in the same manner as therein, or by combining the method with any other known method, compounds of the following Production Examples 12 to 33 can be produced.

PRODUCTION EXAMPLE 12

Production of 5-methyl-6-[5-(methylamino)pyridine-3-yl]-3-phenylisoxazolo[4,5-c]pyridin-4(5H)-one

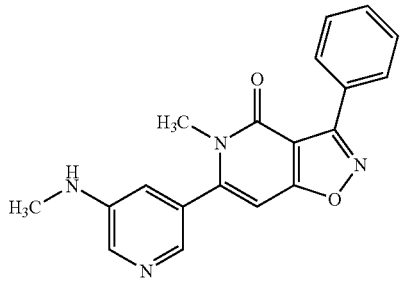

The NMR and Mass data of the compound obtained in Production Example 12 are shown below.

$^1$H NMR (300 Hz, CDCl$_3$) δ ppm: 2.93(3H, brs), 3.45(3H, s), 4.09(1H, m), 6.38(1H, dd, J=2.7, 1.9 Hz), 6.58(1H, s), 7.48–7.56(3H, m), 8.00(1H, d, J=1.9 Hz), 8.16(1H, d, J=2.7 Hz), 8.26–8.30(2H, m)

ESI-MS(m/e): (M+H)$^+$=333

PRODUCTION EXAMPLE 13

Production of 6-[6-(dimethylamino)pyridin-3-yl]-5-methyl-3-phenylisoxazolo[4,5-c]pyridin-4(5H)-one

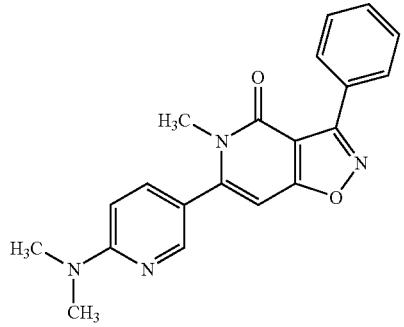

The NMR and Mass data of the compound obtained in Production Example 13 are shown below.

$^1$H NMR (300 Hz, CDCl$_3$) δ ppm: 3.18(6H, s), 3.49(3H, s), 6.53(1H, s), 6.60(1H, dd, J=8.9, 0.8 Hz), 7.47(1H, d, J=8.9 Hz), 7.48–7.55(3H, m), 8.24(1H, d, J=0.8 Hz), 8.25–8.31(2H, m)

ESI-MS(m/e): (M+H)$^+$=347

PRODUCTION EXAMPLE 14

Production of 6-(5-methoxypyridin-2-yl)-5-methyl-3-phenylisoxazolo-[4,5-c]pyridin-4(5H)-one

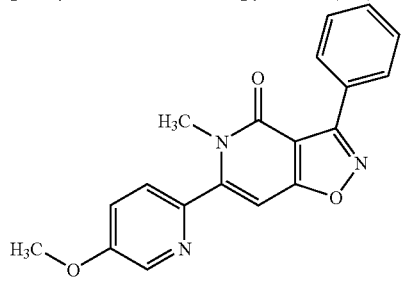

The NMR and Mass data of the compound obtained in Production Example 14 are shown below.

hu 1H NMR (300 Hz, CDCl$_3$) δ ppm: 3.50(3H, s), 3.96(3H, s), 6.62(1H, s), 7.35(1H, dd, J=8.6, 2.9 Hz), 7.48–7.55(4H, m), 8.29(2H, m), 8.45(1H, d, J,2.9 Hz)

ESI-MS(m/e): (M+H)$^+$=334

PRODUCTION EXAMPLE 15

Production of 6-(6-methoxypyridin-3-yl)-5-methyl-3-phenylisoxazolo-[4,5-c]pyridin-4(5H)-one

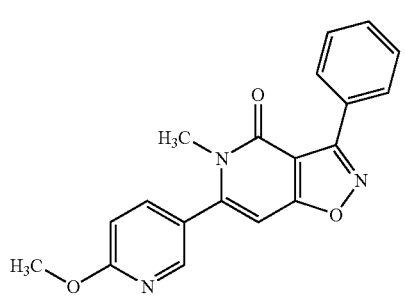

The NMR and Mass data of the compound obtained in Production Example 15 are shown below.

$^1$H NMR (300 Hz, CDCl$_3$) δ ppm: 3.45(3H, s), 4.03(3H, s), 6.55(1H, s), 6.90(1H, d, J=8.6 Hz), 7.52(3H, m), 7.62(1H, dd, J=8.6, 2.5 Hz), 8.25–8.30(3H, m)

ESI-MS(m/e): (M+H)$^+$=334

PRODUCTION EXAMPLE 16

Production of 6-(4-methoxypyridin-2-yl)-5-methyl-3-phenylisoxazolo-[4,5-c]pyridin-4(5H)-one

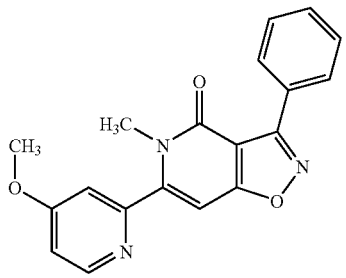

NMR and Mass data of the compound obtained in Production Example 16 are shown below.

$^1$H NMR (300 MHz, CDCl$_3$) δ ppm: 3.48(3H, s), 3.94 (3H, s), 6.64(1H, s), 6.93(1H, dd, J=5.5, 2.1 Hz), 7.04(1H, d, J=2.1Hz), 7.51(3H, m), 8.29(2H, m), 8.57(1H, d, J=5.5 Hz)

ESI-MS(m/e): (M+H)$^+$=334

PRODUCTION EXAMPLE 17

Production of 6-(6-methoxypyridin-2-yl)-5-methyl-3-phenylisoxazolo-[4,5-c]pyridin-4(5H)-one

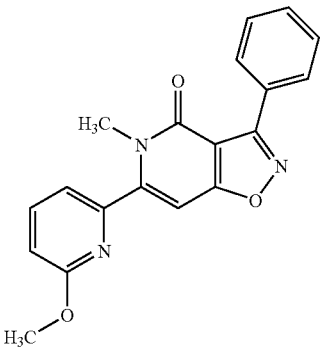

The NMR and Mass data of the compound obtained in Production Example 17 are shown below.

$^1$H NMR (300 Hz, CDCl$_3$) δ ppm: 3.54(3H, s), 3.95(3H, s), 6.66(1H, s), 6.89(1H, dd, J=8.4, 0.8), 7.12(1H, dd, J=7.2, 0.8 Hz), 7.50–7.55(3H, m), 7.74(1H, dd, J=8.4, 7.2 Hz), 8.27–8.32(2H, m)

ESI-MS(m/e): (M+H)$^+$=334

PRODUCTION EXAMPLE 18

Production of 6-(1,3-benzodioxol-5-yl)-5-methyl-3-phenylisoxazolo-4,5-c]pyridin-4(5H)-one

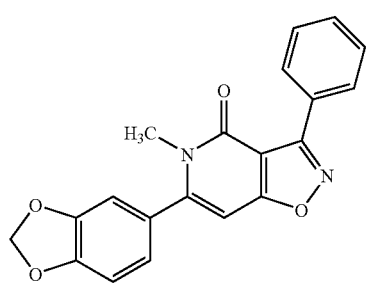

The NMR and Mass data of the compound obtained in Production Example 18 are shown below.

$^1$H NMR (300 MHz, CDCl$_3$) δ ppm: 3.44(3H, s), 6.08 (2H, s), 6.53(1H, s), 6.85(1H, dd, J=1.7, 0.7 Hz), 6.88(1H, d, J=7.9, 1.7 Hz), 6.93(1H, dd, J=7.9, 0.7 Hz), 7.49–7.55 (3H, m), 8.27–8.31(2H, m)

ESI-MS(m/e): (M+H)$^+$=347

PRODUCTION EXAMPLE 19

Production of 6-(3-bromo-4-methoxyphenyl)-5-methyl-3-phenylisoxazolo-[4,5-c]pyridin-4(5H)-one

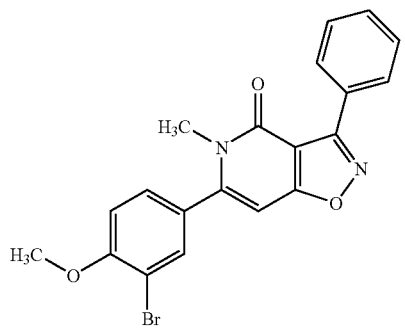

The NMR and Mass data of the compound obtained in Production Example 19 are shown below.

$^1$H NMR (300 MHz, CDCl$_3$) δ ppm: 3.44(3H, s), 4.00 (3H, s), 6.54(1H, s), 7.03(1H, d, J=8.5 Hz), 7.35(1H, dd, J=8.5, 2.2 Hz), 7.50–7.56(3H, m), 7.63(1H, d, J=2.2 Hz), 8.28–8.31(2H, m)

ESI-MS(m/e): (M+H)$^+$=412

PRODUCTION EXAMPLE 20

Production of 5-methyl-3-phenyl-6-[3-(trifluoromethyl)phenyl]-isoxazolo[4,5-c]pyridin-4(5H)-one

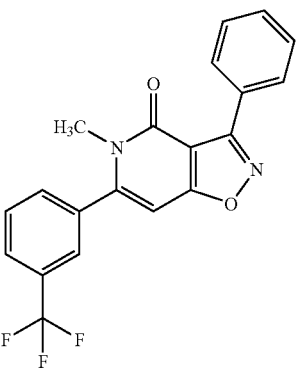

The NMR and Mass data of the compound obtained in Production Example 20 are shown below.

$^1$H NMR (300 MHz, CDCl$_3$) δ ppm: 3.41(3H, s), 6.58 (1H, s), 7.49–7.55(3H, m), 7.63(1H, m), 7.66–7.72(2H, m), 7.82(1H, dd, J=8.8, 2.0Hz), 8.27–8.32(2H, m)

ESI-MS(m/e): (M+H)$^+$=371

PRODUCTION EXAMPLE 21

Production of 5-methyl-3-phenyl-6-[4-propylphenyl]-isoxazolo-[4,5-c]pyridin-4(5H)-one

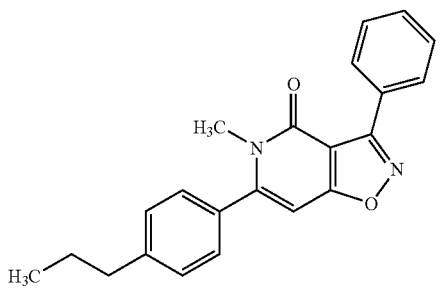

The NMR and Mass data of the compound obtained in Production Example 21 are shown below.

$^1$H NMR (300 MHz, CDCl$_3$) δ ppm: 0.99(3H, t, J=7.3 Hz), 1.70(2H, m), 2.68(2H, t, J=7.6 Hz), 3.43(3H, s), 6.54(1H, s), 7.32(4H, m), 7.48–7.54(3H, m), 8.27–8.32(2H, m) ESI-MS(m/e): (M+H)$^+$=345

PRODUCTION EXAMPLE 22

Production of 6-(2,3-dihydro-1-benzofuran-7-yl)-5-methyl-3-phenylisoxazolo[4,5-c]pyridin-4(5H)-one

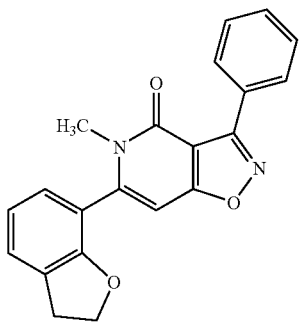

The NMR and Mass data of the compound obtained in Production Example 4 are shown below.

$^1$H NMR (300 MHz, CDCl$_3$) δ ppm: 3.32(2H, t, J=8.8 Hz), 3.45(3H, s), 4.64(2H, t, 8.8 Hz), 6.56(1H, s), 6.98(1H, t, J=7.3 Hz), 7.11(1H, dd, J=7.3, 1.2 Hz), 7.37(1H, dd, J=7.3, 1.2 Hz), 7.48–7.55(3H, m), 8.26–8.32(2H, m)
ESI-MS(m/e): (M+H)$^+$=345.

PRODUCTION EXAMPLE 23

Production of 6-(4-isopropoxyphenyl)-5-methyl-3-phenylisoxazolo-[4,5-c]pyridin-4(5H)-one

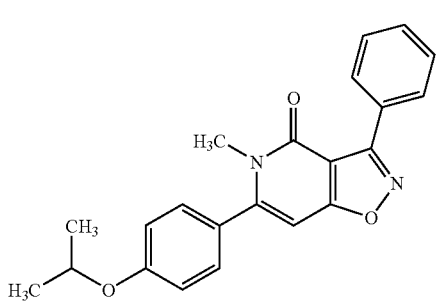

The NMR and Mass data of the compound obtained in Production Example 23 are shown below.

$^1$H NMR (300MHz, CDCl$_3$) δ ppm: 1.40(6H, d, J=6.1 Hz), 3.44(3H, s), 4.64(1H, sex, 6.1 Hz), 6.53(1H, s), 7.00 (2H, d, J=8.8 Hz), 7.31(2H, d, J=8.8 Hz), 7.47–7.57(3H, m), 8.27–8.33(2H, m)

ESI-MS(m/e): (M+H)$^+$=361

PRODUCTION EXAMPLE 24

Production of 6-(1-benzofuran-2-yl)-5-methyl-3-phenylisoxazolo-[4,5-c]pyridin-4(5H)-one

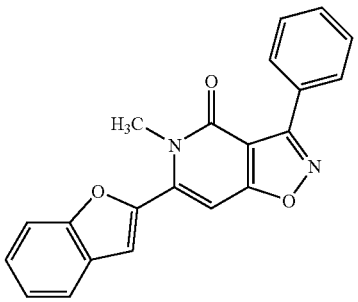

The NMR and Mass data of the compound obtained in Production Example 24 are shown below.

$^1$H NMR (300 MHz, CDCl$_3$) δ ppm: 3.73(3H, s), 7.01 (1H, s), 7.18(1H, d, J=0.9 Hz), 7.36(1H, ddd, J=7.6, 7.2, 0.9 Hz), 7.45(1H, ddd, J=8.3, 7.2, 1.3 Hz), 7.53(3H, m), 7.58 (1H, m), 7.70(1H, dt, J=8.3, 0.9 Hz), 8.27–8.31(2H, m)

ESI-MS(m/e): (M+H)$^+$=343

PRODUCTION EXAMPLE 25

Production of 6-[4-(dimethylamino)phenyl]-5-methyl-3-phenylisoxazolo-[4,5-c]pyridin-4(5H)-one

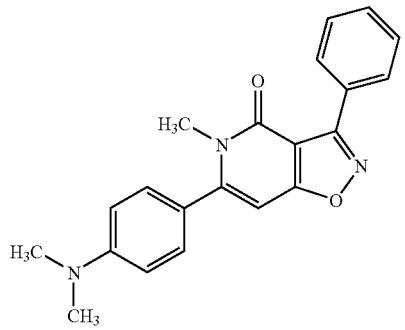

The NMR and Mass data of the compound obtained in Production Example 25 are shown below.

$^1$H NMR (300 MHz, CDCl$_3$) δ ppm: 3.05(6H, s), 3.48 (3H, s), 6.52(1H, s), 6.78(2H, d, J=8.9 Hz), 7.27(2H, d, J=8.9 Hz), 7.49–7.56(3H, m), 8.28–8.32(2H, m)

ESI-MS(m/e): (M+H)$^+$=346

PRODUCTION EXAMPLE 26

Production of 6-(3-fluoro-4-methoxyphenyl)-5-methyl-3-phenylisoxazolo-[4,5-c]pyridin-4(5H)-one

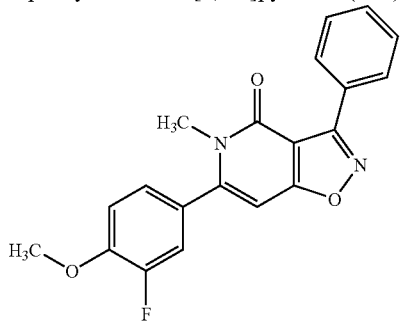

The NMR and Mass data of the compound obtained in Production Example 26 are shown below.

$^1$H NMR (300 MHz, CDCl$_3$) δ ppm: 3.43(3H, s), 3.98 (3H, s), 6.53(1H, s), 7.06–7.18(3H, m), 7.49–7.55(3H, m), 8.26–8.32(2H, m)

ESI-MS(m/e): (M+H)$^+$=351

PRODUCTION EXAMPLE 27

Production of 6-[3-(dimethylamino)phenyl]-5-methyl-3-phenylisoxazolo-[4,5-c]pyridin-4(5H)-one

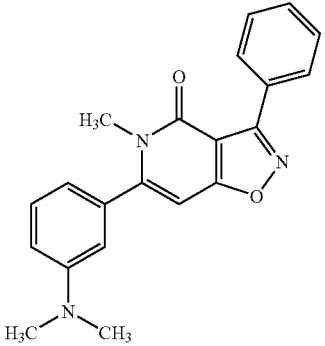

The NMR and Mass data of the compound obtained in Production Example 27 are shown below.

$^1$H NMR (300 MHz, CDCl$_3$) δ ppm: 3.01(6H, s), 3.44 (3H, s), 6.57(1H, s), 6.65(1H, dd, J=0.9, 0.8 Hz), 6.68(1H, dd, J=7.5, 0.9 Hz), 6.83(1H, dd, J=8.5, 0.8 Hz), 7.34(1H, dd, J=8.5, 7.5 Hz), 7.49–7.55(3H, m), 8.28–8.32(2H, m)

ESI-MS(m/e): (M+H)$^+$=346

PRODUCTION EXAMPLE 28

Production of 3-(5-methyl-4-oxo-3-phenyl-4,5-dihydroisoxazolo-[4,5-c]pyridin-6-yl) benzonitrile

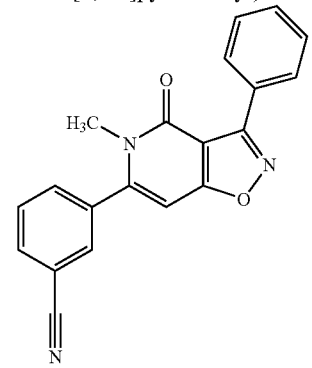

The NMR and Mass data of the compound obtained in Production Example 28 are shown below.

$^1$H NMR (300 MHz, CDCl$_3$) δ ppm: 3.39(3H, s), 6.54 (1H, s), 7.47–7.56(3H, m), 7.64–7.71(2H, m), 7.72(1H, dd, J=9.5, 1.2 Hz), 7.88–7.90(1H, m), 8.24–8.31(2H, m)

ESI-MS(m/e): (M+H)$^+$=328

PRODUCTION EXAMPLE 29

Production of 6-(3-methoxyphenyl)-5-methyl-3-phenylisoxazolo[4,5-c]pyridin-4(5H)-one

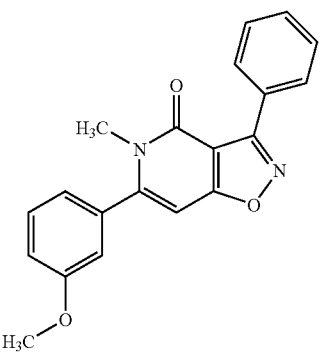

The NMR and Mass data of the compound obtained in Production Example 29 are shown below.

$^1$H NMR (300 MHz, CDCl$_3$) δ ppm: 3.42(3H, s), 3.87 (3H, s), 6.56(1H, s), 6.91(1H, m), 6.98(1H, m), 7.07(1H, m), 7.44(1H, dd, J=8.1, 7.8 Hz), 7.49–7.55(3H, m), 8.27–8.32 (2H, m)

ESI-MS(m/e): (M+H)$^+$=333

PRODUCTION EXAMPLE 30

Production of 6-(5-methoxypyridin-3-yl)-5-methyl-3-phenylisoxazolo-[4,5-c]pyridin-4(5H)-one

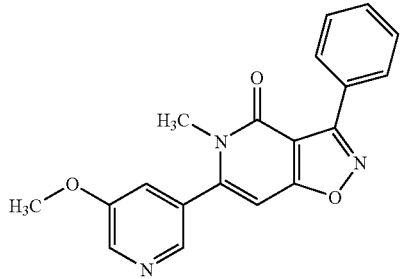

The NMR and Mass data of the compound obtained in Production Example 30 are shown below.

$^1$H NMR (300 MHz, CDCl$_3$) δ ppm: 3.43(3H, s), 3.95 (3H, s), 6.58(1H, s), 7.23(1H, dd, J=2.8, 1.8 Hz), 7.49–7.57 (3H, m), 8.26–8.32(3H, m), 8.48(1H, d, J=2.8 Hz)

ESI-MS(m/e): (M+H)$^+$=333

PRODUCTION EXAMPLE 31

Production of 5-methyl-3-phenyl-6-pyridin-2-yl-isoxazolo[4,5-c]-pyridin-4(5H)-one

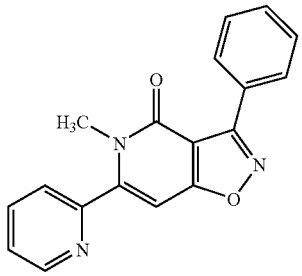

The NMR and Mass data of the compound obtained in Production Example 31 are shown below.

$^1$H NMR (300 MHz, CDCl$_3$) δ ppm: 3.49(3H, s), 6.65 (1H, s), 7.46(1H, ddd, J=7.7, 4.8, 1.0 Hz), 7.49–7.57(4H, m), 7.90(1H, dt, J=1.8, 7.7 Hz), 8.26–8.31(2H, m), 8.78(1H, ddd, J=4.8, 1.8, 1.0 Hz)

ESI-MS(m/e): (M+H)$^+$=304

PRODUCTION EXAMPLE 32

Production of 5-methyl-6-pyridin-3-yl-3-pyridin-4-yl-isoxazolo[4,5-c]-pyridin-4(5H)-one

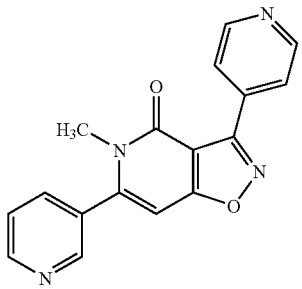

The NMR and Mass data of the compound obtained in Production Example 32 are shown below.

$^1$H NMR (300 MHz, CDCl$_3$) δ ppm: 3.45(3H, s), 6.62 (1H, s), 7.48–7.54(1H, m), 7.75–7.81(1H, m), 8.28(2H, d, J=6.2 Hz), 8.74(1H, dd, J=2.3, 0.8 Hz), 8.78–8.84(3H, m)

ESI-MS(m/e): (M+H)$^+$=305

PRODUCTION EXAMPLE 33

Production of 5-methyl-6-pyridin-2-yl-3-pyridin-4-yl-isoxazolo[4,5-c]-pyridin-4(5H)-one

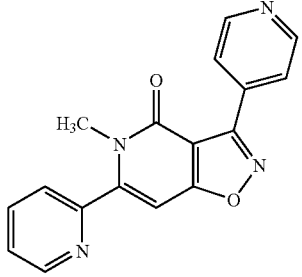

The NMR and Mass data of the compound obtained in Production Example 33 are shown below.

$^1$H NMR (300 MHz, CDCl$_3$) δ ppm: 3.51(3H, s), 6.62 (1H, s), 7.46–7.51(1H, m), 7.53–7.58(1H, m), 7.90–7.96 (1H, m), 8.28(2H, d, J=6.2 Hz),8.74(1H, dd, J=2.3, 0.8 Hz), 8.78–8.84(2H, m)

ESI-MS(m/e): (M+H)$^+$=305

The compounds of Production Examples 20, 22, 24, 25, 26, 27, 28, 29 and 31 were purified through fractional thin-layer chromatography (Kieselgel™ 60F254, Art5744 (by Merck) with hexane/ethyl acetate=1/1).

REFERENCE EXAMPLE 1

Production of pyridin-4-aldoxime

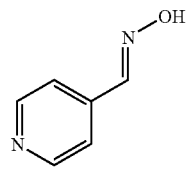

Isonicotinaldehyde (5.4 g, 50 mmols) and hydroxylamine hydrochloride (4.2 g, 61 mmols) were dissolved in a mixed solvent of MeOH and water, and the reaction liquid was heated under reflux for 5 hours. After this was cooled, the solvent was evaporated away under reduced pressure. Aqueous saturated sodium bicarbonate solution was added to the residue, to which ethyl acetate was added for organic layer extraction. The collected organic layer was dried with magnesium sulfate, and the solvent was evaporated away under reduced pressure to obtain the entitled compound (5.6 g, yield 94%). For the compound, pyridin-4-aldoxime, a commercial product may also be used.

The NMR data of the compound obtained in Reference Example 1 are shown below.

$^1$H NMR (200 MHz, CDCl$_3$) δ ppm: 7.51(d, J=6.1 Hz, 2H), 8.12(s, 1H), 8.64(d, J=6.1 Hz, 2H)

REFERENCE EXAMPLE 2

Production of ethyl 3-pyrrolidinocrotonate

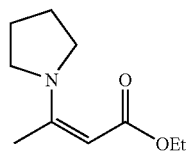

Ethyl acetacetate (13 ml, 102 mmols) and pyrrolidine (8.5 ml, 102 mmols) were dissolved in toluene and mixed in azeotropy for 2 hours. Next, the solvent was removed under reduced pressure to obtain the entitled compound (18.3 g, yield 98%). For the compound, ethyl 3-pyrrolidinocrotonate, a commercial product may also be used.

The NMR data of the compound obtained in Reference Example 2 are shown below.

$^1$H NMR (200 MHz, CDCl$_3$) δ ppm: 1.25(t, J=7.2 Hz, 3H), 1.83–2.03(m, 4H), 2.46(s, 3H), 3.20–3.43(m, 4H), 4.09(q, J=7.2 Hz, 2H), 4.47(s, 1H)

REFERENCE EXAMPLE 3

Production of N-methyl-3-pyrrolidine-crotonamide

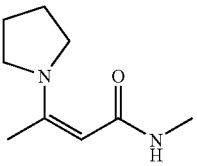

An aqueous solution of methylacetacetamide (1.5 g, about 13 mmols) was dissolved in toluene (20 ml), and pyrrolidine (1.6 ml, 20 mmols) was added to it at room temperature, and then heated under reflux for 2 hours. The reaction liquid was cooled to 0 degree, and the solid thus formed was taken out through filtration, washed and dried under reduced pressure to obtain 1.1 g of the intended product (6.5 mmols, 50%).

The NMR and Mass data of the compound obtained in Reference Example 3 are shown below.

$^1$H NMR (CDCl3, 400 MHz) δ ppm: 1.88–1.92(m, 4H), 2.50(s, 3H), 2.79(d, J=5.2 Hz, 3H), 3.24(br, 4H), 4.30(s, 1H), 4.90(br, 1H)

ESI-MS(m/e): (M+H)$^+$=169

REFERENCE EXAMPLE 4

Production of
4-ethoxycarbonyl-5-methyl-3-pyridin-4-yl-isoxazole

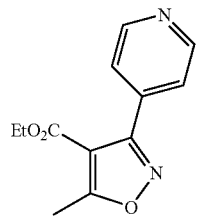

N-chlorosuccinimide (2.66 g, 20 mmols) was dissolved in chloroform (12 ml), and pyridine (0.125 ml) and a chloroform solution (36 ml) of pyridin-4-aldoxime (2.4 g) obtained in Reference Example 1 were added to it at room temperature and stirred for 30 minutes. Next, a chloroform solution (2 ml) of ethyl 3-pyrrolidinocrotonate (3.6 g, mmols) obtained in Reference Example 2 was added to it, and the reaction solution was then heated up to 50 degrees. A chloroform solution (9 ml) of triethylamine (2.7 ml) was dropwise added to it over a period of 1 hour, and then stirred overnight at 50° C. The reaction liquid was cooled to room temperature, and transferred into aqueous saturated sodium bicarbonate solution and extracted with chloroform. The organic layer collected was dried with magnesium sulfate, and this was concentrated under reduced pressure to remove the solvent. The resulting residue was purified through silica gel column chromatography (Wakogel® C-300 with eluent solvent of hexane-ethyl acetate (3:1)) to obtain the entitled compound as a mixture of isomers thereof (18 g, yield 39%).

The NMR data of the compound obtained in Reference Example 4 are shown below.

$^1$H NMR (300 MHz, CDCl$_3$) δ ppm: 1.25(t, J=7.2 Hz, 3H), 2.76(s, 3H), 4.27(q, J=7.2 Hz, 2H), 7.56(d, J=6.0 Hz, 2H), 8.72(d, J=6.0 Hz, 2H)

REFERENCE EXAMPLE 5

Production of
5-methyl-3-pyridin-4-yl-4-isoxazole-carboxylic acid

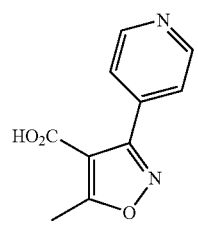

4-ethoxycarbonyl-5-methyl-3-pyridin-4-yl-isoxazole obtained in Reference Example 4 was dissolved in MeOH (3 ml), and aqueous 3 M sodium hydroxide solution (5 ml) was added to the reaction liquid. Then, the reaction mixture was stirred at room temperature for 2 hours. Next, aqueous 1 M HCl solution (15 ml) was added to the reaction liquid with cooling with ice to thereby neutralize the reaction liquid. The solid formed was taken out through filtration, washed with water, and dried under reduced pressure to obtain the entitled compound (1.3 g, yield 82%).

The NMR and Mass data of the compound obtained in Reference Example 5 are shown below.

$^1$H NMR (300 MHz, CD$_3$OD) δ ppm: 2.71(s, 3H), 7.74 (br, 2H), 8.62(br, 2H)

ESI-MS(m/e): (M-H)$^-$=204

REFERENCE EXAMPLE 6

Production of
N,5-dimethyl-3-phenyl-4-isoxazolecarboxamide

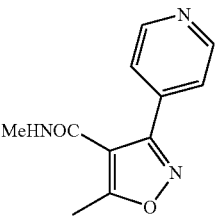

5-Methyl-3-pyridin-4-yl-4-isoxazole-carboxylic acid (500 mg, 2.5 mmols) obtained in Reference Example 5 was dissolved in N,N-dimethylformamide (10 ml), and methylamine hydrochloride (333 mg, 4.9 mmols), HOBt (496 mg, 3.7 mmols), WSC (702 mg, 3.7 mols) and triethylamine (1.02 ml, 7.3 mmols) were added to the solution. The reaction mixture was stirred at room temperature for 5 hours. The reaction liquid was transferred into aqueous saturated sodium bicarbonate solution, and ethyl acetate was added thereto for organic layer extraction. The liquid extract was washed with aqueous saturated sodium bicarbonate solution, and the organic layer was dried with magnesium sulfate. Then, the solvent was removed under reduced pressure, and the resulting residue was purified through silica gel column chromatography to obtain the entitled compound (360 mg, yield 66%).

In addition, the compound of Reference Example 6 may also be produced according to the following method.

N-chlorosuccinimide (292 mg, 2.2 mmols) was dissolved in chloroform (6 ml), and pyridine (0.040 ml) and a chloroform solution (6 ml) of pyridin-4-aldoxime (2.4 g) obtained in Reference Example 1 were added thereto at room temperature, and stirred at 50 degrees for 30 minutes. Next, methyl-3-pyrrolidinocrotonamide (244 mg. 2 mmols) obtained in Reference Example 3 was added to it at room temperature, and the reaction solution was heated up to 50 degrees. Then, triethylamine (0.306 ml) was dropwise added to it over a period of 10 minutes, and then stirred at 50° C. for 3 hours. The reaction liquid was cooled to room temperature, then transferred into aqueous saturated sodium bicarbonate solution, and extracted with chloroform. The organic layer collected was dried with magnesium sulfate, the solvent was removed under reduced pressure, and the resulting residue was purified through silica gel column chromatography (Wakogel® C-300 with eluent solvent of chloroform-methanol (20:1)) to obtain the entitled compound (242 mg, yield 56%).

The NMR and Mass data of the compound obtained in Reference Example 6 are shown below.

$^1$H NMR (300 MHz, CD$_3$OD) δ ppm: 2.68(s, 3H), 2.89(d, J=4.7 Hz, 3H), 5.50(br, 1H), 7.58(brd, J=5.0 Hz, 2H), 8.75(brd, J=5.0 Hz, 2H)
ESI-MS(m/e): (M+H)$^+$=218

REFERENCE EXAMPLE 7

Production of 5-(4-methoxyphenylcarbonylmethyl)-3-(pyridin-4-yl)-N-methyl-4-isoxazolecarboxamide

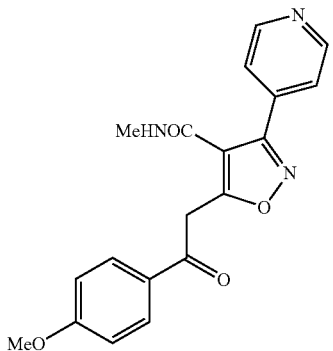

N,5-dimethyl-3-phenyl-4-isoxazolecarboxamide (100 mg, 0.46 mols) obtained in Reference Example 6 was dissolved in dewatered THF (3 ml) in a nitrogen atmosphere, and the reaction liquid was cooled to −78° C. N-BuLi (0.75 ml, 1.2 mmols) was dropwise added to the reaction liquid, and the reaction liquid was stirred at −78° C. for 1.5 hours. Next, a THF solution (1 ml) of methyl paramethoxybenzoate (191 mg, 1.2 mmols) was added to the reaction liquid. The reaction mixture was stirred at −78° C. for 1 hour, and then transferred into aqueous saturated sodium bicarbonate solution. An organic layer was extracted out of it with chloroform added thereto. The organic layer was dried with magnesium sulfate, then the solvent was evaporated away under reduced pressure, and the residue was purified through silica gel column chromatography (Wakogel® C-300 with eluent solvent of chloroform-MeOH (30:1)) to obtain the entitled compound (52 mg, yield 32%).

The NMR and Mass data of the compound obtained in Reference Example 7 are shown below.
$^1$H NMR (CDCl3, 300 MHz ) δ ppm: 2.92(d, J=4.8 Hz, 3H), 3.92(s, 3H), 4.64(s, 2H), 7.02(d, J=8.8 Hz, 2H), 7.13–7.20(br, 1H), 7.70–7.72(m, 2H), 8.07(d, J=8.8 Hz, 2H), 8.73–8.74(m, 2H)
ESI-MS(m/e): (M+H)$^+$=352

REFERENCE EXAMPLE 8

Production of Compound (II)

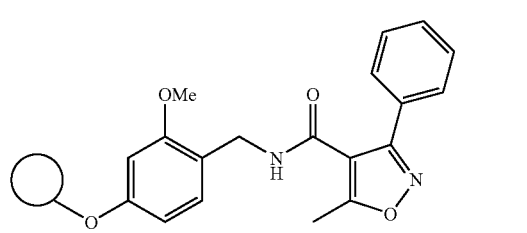

wherein each symbol has the same meaning as above:
5.0 g of commercially-available ArgoGel-MB-CHO Resin® (0.4 mmol/g) was suspended in DMF (20 ml) and ACOH (1.0 ml), and then methylamine hydrochloride (405 mg) and NaBH (OAc)$_3$ (2.12 g) were added thereto in order, and stirred at room temperature for 12 hours. The reaction mixture was filtered, and the residual resin was washed with DMF, MeOH, THF and methylene chloride in that order twice each, and then dried. Dewatered methylene chloride (30 ml) was added to the thus-obtained resin to suspend it therein, and then N,N-diisopropylethylamine (5.2 ml), 5-methyl-3-phenylisoxazole-4-carboxylic acid (2.03 g) and DMC (1.70 g) were added thereto in that order, and stirred at room temperature for 1 hour. The reaction mixture was filtered, and the residual resin was washed with DMF, MeOH, THF and methylene chloride twice each, and then dried to obtain the resin of formula (II).

Formulation Examples of the compounds of the invention are mentioned below, to which, however, the preparations of the compounds of the invention are not limited.

FORMULATION EXAMPLE 1

10 parts of the compound of Production Example 1, 15 parts of heavy magnesium oxide and 75 parts of lactose were uniformly mixed to form a powdery or granular preparation having a size of at most 350 μm. The preparation was encapsulated into capsules.

FORMULATION EXAMPLE 2

45 parts of the compound of Production Example 1, 15 parts of starch, 16 parts of lactose, 21 parts of crystalline cellulose, 3 parts of polyvinyl alcohol and 30 parts of distilled water were uniformly mixed, ground, granulated, dried and then dressed into granules having a diameter of from 1410 to 177 μm.

FORMULATION EXAMPLE 3

A granular preparation was produced in the same manner as in Formulation Example 2. 3 parts of calcium stearate was added to 96 parts of the granular preparation, and tabletted under compression into tablets having a diameter of 10 mm.

FORMULATION EXAMPLE 4

10 parts of crystalline cellulose and 3 parts of calcium stearate were added to 90 parts of the granular preparation obtained in Formulation Example 2, and tabletted under compression into tablets having a diameter of 8 mm. These were coated with a mixture suspension of syrup, gelatin and precipitating calcium carbonate into sugar-coated tablets.

INDUSTRIAL APPLICABILITY

The compounds of formula [I-a] or their pharmaceutically-acceptable salts have a metabotropic glutamic acid receptor-antagonistic effect, and are therefore useful for remedy and/or prevention of, for example, anxiety disorders, psychosomatic disorders, obsessive-compulsive neurosis, bipolar disorders, melancholia, eating disorders, schizophrenia, multi-infarct dementia, Alzheimer disease, epilepsy, Parkinson disease, Huntington's chorea, pain or retrograde neurosis.

What is claimed is:

1. An isoxazolopyridone compound of a formula (I-a), or a pharmaceutically-acceptable salt thereof:

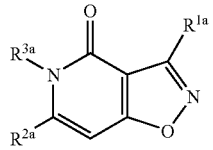

[I-a]

wherein $R^{1a}$ represents an optionally-substituted heteroaryl group, $R^{2a}$ represents an optionally-substituted phenyl or heteroaryl group, and $R^{3a}$ represents a methyl group, wherein the heteroaryl group is a 4- to 7-membered monocyclic group having from 1 to 3 hetero atoms selected from the group consisting of oxygen atom, sulfur atom, and nitrogen atom, or a condensed heteroaryl group of the monocyclic group that is condensed with a benzene or pyridine ring, and wherein the heteroaryl, phenyl, or condensed heteroaryl groups are optionally substituted with substituents comprising a lower alkyl group, a nitro group, a halogen atom, an amino group, a cyano group, a hydroxyl group, a lower alkoxy group, a carboxyl group, a carbamoyl group, a lower alkylcarbamoyl group, a di-lower alkylcarbamoyl group, a di-lower alkylamino group, and a lower alkylamino group.

2. An isoxazolopyridone compound or a pharmaceutically-acceptable salt thereof as claimed in claim 1, wherein $R^{1a}$ is an optionally-substituted heteroaryl group selected from the group consisting of a furyl group, a thienyl group, a pyrrolyl group, an imidazolyl group, a pyrazolyl group, an isothiazolyl group, an isoxazolyl group, a pyridyl group, a pyrimidinyl group, a quinolyl group, an isoquinolyl group, a quinazolyl group, a quinolidinyl group, a quinoxalinyl group, a cinnolinyl group, a benzimidazolyl group, an imidazopyridyl group, a benzofuranyl group, a naphthyridinyl group, a 1,2-benzisoxazolyl group, a benzoxazolyl group, a benzothiazolyl group, an oxazolopyridyl group, an isothiazolopyridyl group, and a benzothienyl group.

3. The isoxazolopyridone compound or a pharmaceutically-acceptable salt thereof as claimed in claim 1, wherein $R^{1a}$ is an optionally-substituted pyridyl group.

4. The isoxazolopyridone compound or a pharmaceutically-acceptable salt thereof as claimed in claim 1, wherein $R^{1a}$ is a 4-pyridyl group, and $R^{2a}$ is a methoxy-substituted phenyl or pyridyl group.

5. The isoxazolopyridone compound or a pharmaceutically-acceptable salt thereof as claimed in claim 1, wherein $R^{2a}$ is an unsubstituted phenyl group.

6. The isoxazolopyridone compound or a pharmaceutically-acceptable salt thereof as claimed in claim 1, wherein $R^{1a}$ is a 4-pyridyl group, and $R^{2a}$ is a 3-methoxyphenyl or 4-methoxyphenyl group.

7. The isoxazolopyridone compound or a pharmaceutically-acceptable salt thereof as claimed in claim 1, wherein $R^{2a}$ is a 5-methoxy-3-pyridyl, 3-methoxy-4-pyridyl, 5-dimethylamino-3-pyridyl, 3,4-methylenedioxyphenyl or 5-methoxy-2-pyridyl group.

8. The compound according to claim 1, wherein the compound represented by formulat (I-a) is: 5-methyl-6-(4-methoxyphenyl)-3-pyridin-4-yl-isoxazolo[4,5-c]pyridin-4(5H) one, 5-methyl-3-pyridin-4-yl-6-phenylisoxazolo[4,5-c]pyridin-4(5H)-one,5-methyl-3-pyridin-2-yl-6-phenylisoxazolo[4,5-c]pyridin-4(5H)-one,5-methyl-3-pyridin-3-yl-6-phenylisoxazolo[4,5-c]pyridin-4(5H)-one,5-methyl-6-(3-methoxyphenyl)-3-pyridin-4-yl-isoxazolo[4,5-c]pyridin-4(5H)-one,5-methyl-6-pyridin-3-yl-3-pyridin-4-yl-isoxazolo[4,5-c]pyridin-4(5H)-one, or 5-methyl-6-pyridin-2-yl-3-pyridin-4-yl-isoxazolo[4,5-c]pyridin-4(5H)-one.

* * * * *